March 3, 1959 H. C. SWIM Plant Pat. 1,814
ROSE PLANT
Filed Feb. 26, 1958
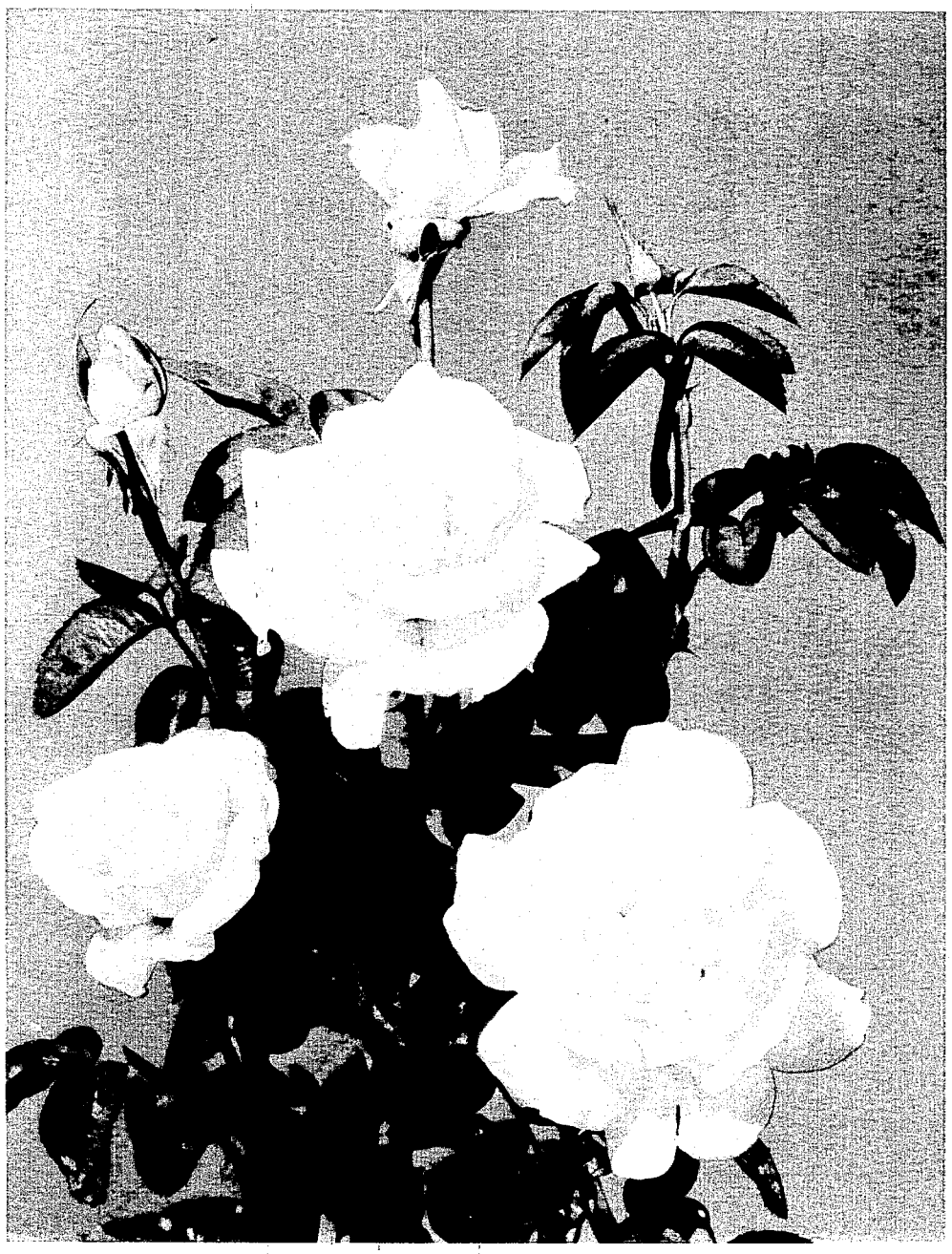
Inventor.
H. C. Swim
By: Robb & Robb
Attorneys.

United States Patent Office

Plant Pat. 1,814
Patented Mar. 3, 1959

1,814

ROSE PLANT

Herbert C. Swim, Ontario, Calif., assignor to Armstrong Nurseries, Inc., Ontario, Calif., a corporation of California Application February 26, 1958, Serial No. 717,795

1 Claim. (Cl. 47—61)

The present invention relates to a new and distinct variety of rose plant of the hybrid tea class, which was originated by me by crossing the variety "Charlotte Armstrong" (Plant Patent No. 455) with the variety "Peace" (Plant Patent No. 591).

The primary objective of this breeding was to produce a new rose variety which combines therein the most desirable characteristics of the parent varieties. This objective was fully achieved, along with other improvements, as evidenced by the following unique combination of characteristics which are outstanding in the new variety:

(1) A vigorous and relatively floriferous habit of growth;

(2) The habit of bearing its flowers on single stems of a length ranging from medium to long;

(3) A graceful, urn-shaped bud form, with the form of the half-open flowers approaching that of the parent "Charlotte Armstrong," and the form of the open flowers approaching that of the parent "Peace";

(4) Large, double flowers; and (5) A distinctive general color tonality of the flowers ranging between White and Pale Yellow, and often tinged with Pale Pink.

The foregoing characteristics definitely differentiate my new variety from its parents, as well as from all other varieties of its class of which I am aware. In comparison with its seed parent, "Charlotte Armstrong," the new variety is somewhat less vigorous, but its flowers range in color between White and Pale Yellow, often with tinges of Pale Pink, whereas the flowers of this parent range in color from Blood Red to Cerise. As compared with its pollen parent, "Peace," the new variety is more vigorous, more floriferous, its average flower stem length is somewhat shorter, the form of the buds is generally more slender and urn-shaped, the flowers have fewer petals, and while the flowers are somewhat similar in color to those of this parent, the shades of Yellow and Pink are lighter.

Asexual reproduction of my new variety by budding, as performed at Ontario, California, show that the aforesaid characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated as "Wilson") and Robert Ridgway's Color Standards and Nomenclature (herein after abbreviated as "Ridgway") as indicated, except where general color terms of ordinary dictionary significance are obvious:

Type: Bush; outdoor; seedling; for cut flowers and for garden decoration.

Class: Hybrid tea.

Breeding: Seedling.

*Seed parent.*—"Charlotte Armstrong."

*Pollen parent.*—"Peace."

Propagation: Holds its distinguishing characteristics through succeeding propagations by budding.

*Flower*

Locality where grown and observed: Ontario, California.

Flowers borne: Usually singly, but sometimes 2 or 3 to stem; on strong stems of a length ranging from medium to long.

Quantity of bloom: Abundant, outdoors.

Continuity: Nearly continuous during growing season.

Fragrance: Slight.

Bud:

*Peduncle.*—Average length; average caliper; erect; usually smooth. Color—near Biscay Green, Plate XVII (Ridgway).

*Before calyx breaks.*—Size—medium. Form—medium length; ovoid; with foliaceous appendages on the surface of the bud; usually with slender, much-cut foliaceous parts extending beyond the tip of the bud equal to ½ or more of its length.

*As calyx breaks.*—Color—near primrose yellow, Plate 601/1, page 65 (Wilson), often marked with near Mandarin Red, Plate 17/2, page 17 (Wilson) on area first exposed to sun.

*Sepals.*—Inner surface—with fine, wooly tomentum; Margins of alternate sepals lined with fine, wooly tomentum; others lined with stipitate glands. Outer surface—moderately smooth; usually with moderate bloom.

*As first petal opens.*—Size—average. Form—from medium length to long; urn-shaped. Color: outside—between Primrose Yellow, Plate 601/1, page 65 (Wilson) and Primrose Yellow, Plate 601/2, page 65 (Wilson), sometimes marked or flecked with near Azalea Pink, Plate 618/1, page 74 (Wilson), and with small area at base of petal near point of attachment near Empire Yellow, Plate 603, page 66 (Wilson); inside—between Primrose Yellow, Plate 601/1, page 65 (Wilson) and Primrose Yellow, Plate 601/2, page 65 (Wilson), sometimes tinged with near Camellia Rose, Plate 622/3, page 148 (Wilson) toward outer edge of petal, and with small area at base of petal near point of attachment near Empire Yellow, Plate 603, page 66 (Wilson).

*Opening.*—Opens up well; usually not retarded from opening by cold, hot, wet or dry weather.

Bloom:

*Size (when fully open).*—From average to large; from 4 inches to 5 inches.

*Petalage.*—Double; from 24 to 30 petals, plus from 6 to 10 petaloids; arranged regularly.

*Form.*—High-centered and somewhat globular at first, but becoming from cupped to high-centered; petals being at first somewhat tightly cupped, with lateral margins of inner petals usually reflexed slightly from ⅓ to ½ of petal length, and with lateral margins of outer petals usually reflexed from ½ to ¾ of petal length, with apex of both inner and outer petals usually reflexed from ¼ to ½ of petal length; becoming later at maturity somewhat more loosely cupped, with tips and lateral margins reflexed outwardly.

Petals:

*Texture.*—Medium thickness; leathery. Inside—from satiny to velvety. Outside—from slightly shiny to satiny.

*Shape.*—Outer—broadly obovate, with apex flat. Intermediate—obovate, with apex from rounded to flat and sometimes with 1 or 2 notches. Inner—narrowly obovate, with apex rounded, and with 1 or 2 notches.

This description of a newly opened flower was made from a rose grown outdoors in the month of July, at Ontario, California:

*Color.*—Outer petal: outside surface—between White and Primrose Yellow, Plate 601/3, page 65 (Wilson), sometimes flecked with near Camellia Rose, Plate 622/2, page 148 (Wilson), with small area at base of petal near point of attachment near Empire Yellow, Plate 603, page 66 (Wilson); inside surface—between White and Primrose Yellow, Plate 601/3, page 65 (Wilson), often tinged with near Camellia Rose, Plate 622/3, page 148 (Wilson) toward outer edge of petal, with small area at base of petal near point of attachment near Empire Yellow, Plate 603, page 66 (Wilson). Intermediate petal: outside surface—between White and Primrose Yellow, Plate 601/3, page 65 (Wilson), sometimes tinged with near Camellia Rose, Plate 622/3, page 148 (Wilson) toward outer edge of petal, with small area at base of petal near point of attachment near Empire Yellow, Plate 603, page 66 (Wilson); inside surface—between White and Primrose Yellow, Plate 601/3, page 65 (Wilson), often tinged with near Camellia Rose, Plate 622/3, page 148 (Wilson) toward outer edge of petal, with small area at base of petal near point of attachment near Empire Yellow, Plate 603, page 66 (Wilson). Inner petal: outside surface—near Primrose Yellow, Plate 601/3, page 65 (Wilson), often tinged with near Camellia Rose, Plate 622/3, page 148 (Wilson) toward outer edge of petal, with small area at base of petal near point of attachment near Empire Yellow, Plate 603, page 66 (Wilson); inside surface—near Primrose Yellow, Plate 601/3, page 65 (Wilson), often tinged with near Camellia Rose, Plate 622/3, page 148 (Wilson) toward outer edge of petal, with small area at base of petal near point of attachment near Empire Yellow, Plate 603, page 66 (Wilson).

This description was made from a rose that was open for 3 days outdoors in the month of July at Ontario, California:

*Color.*—Outer petal: outside surface—between White and Primrose Yellow, Plate 601/3, page 65 (Wilson), with small area at base of petal near point of attachment near Empire Yellow, Plate 603, page 66 (Wilson); inside surface—between White and Primrose Yellow, Plate 601/3, page 65 (Wilson), often tinged slightly with near Camellia Rose, Plate 622/3, page 148 (Wilson) toward outer edge of petal, with small area at base of petal near point of attachment near Empire Yellow, Plate 603, page 66 (Wilson). Inner petal: outside surface—between White and Primrose Yellow, Plate 601/3, page 65 (Wilson), with small area at base of petal near point of attachment near Empire Yellow, Plate 603, page 66 (Wilson); inside surface—between White and Primrose Yellow, Plate 601/3, page 65 (Wilson), often tinged slightly with near Camellia Rose, Plate 622/3, page 148 (Wilson) toward outer edge of petal, with small area at base of petal near point of attachment near Empire Yellow, Plate 603, page 66 (Wilson).

*General color effect.*—Newly opened flower—Between Empire Yellow, Plate 603/2, page 66 (Wilson) and Empire Yellow, Plate 603/3, page 66

(Wilson), often with tinges of near Peach, Plate 512/3, page 134 (Wilson). 3-days open—between White and Primrose Yellow, Plate 601/3, page 65 (Wilson), often with tinges of near Camellia Rose, Plate 622/3, page 148 (Wilson).

*Behavior.*—Drop off cleanly; not particularly affected by cold, hot, wet or dry weather.

*Flower longevity.*—On bush in garden—4 or 5 days in August. Cut roses grown outdoors and kept at living-room temperatures—4 or 5 days in August.

*Reproductive organs*

Stamens: From few to average number; arranged regularly about pistils; a few mixed with petaloids.

Filaments: From medium length to long; from 5 to 14 mm. in length; most with anthers. Color—near Empire Yellow, Plate 603/1, page 66 (Wilson).

Anthers: From small to medium size; all open approximately at once. Color: upper side—margins near Indian Yellow, Plate 6/2, page 6 (Wilson), with remainder near Lemon Yellow, Plate 4/2, page 4 (Wilson); under side—margins near Indian Yellow, Plate 6/2, page 6 (Wilson), with remainder near Lemon Yellow, Plate 4/2, page 4 (Wilson).

Pollen: Somewhat sparse. Color—near Chinese Yellow, Plate 606, page 68 (Wilson).

Pistils: Many; approximately 140 in number.

Styles: Moderately even; from short to average length; from 4 to 8 mm. long; thin to average caliper; bunched. Color—upper half near Crimson, Plate 22/1, page 22 (Wilson), with remainder near Uranium Green, Plate 63/3, page 63 (Wilson).

Stigma: Color—near Straw Yellow, Plate 604/2, page 67 (Wilson).

Ovaries: Usually all enclosed in calyx, but some protruding from calyx.

Hips: From short to average length; globular; smooth; walls thick and fleshy. Color (half mature)—near Absinthe Green, Plate XXXI (Ridgway).

Sepals: Permanent; medium length; curled and re-curved. Color: inside—near Mytho Green, Plate XLI (Ridgway); outside—near Biscay Green, Plate XVII (Ridgway).

Seeds: Few; from 3 to 10 in number per open-pollinated hip; usually from small to medium size.

*Plant*

Foliage:

*Leaves.*—Compound of usually 5 to 7 leaflets; from normal abundance to abundant; medium size; somewhat leathery; semi-glossy.

*Leaflets.*—Shape—ovoid, with apex acute. Base—round. Margin—simply serrate.

*Color.*—Mature: upper surface—between Deep Dull Yellow-Green, (1), Plate XXXII (Ridgway) and Dark Dull Yellow-Green, Plate XXXII (Ridgway); under surface—near Light Grape Green, Plate XLI (Ridgway). Young: upper surface—near Oil Green, Plate V (Ridgway); under surface—between Prussian Red, Plate XXVII (Ridgway) and Cameo Brown, Plate XXVIII (Ridgway).

*Rachis (the supporting stem of the compound leaf).*—Average size. Upper side—grooved; with some stipitate glands on edges. Under side—moderately smooth; with stipitate glands and 1 or 2 prickles.

*Stipules.*—From short to medium length; medium width; with short points turning out at an angle of more than 45°.

*Disease resistance.*—Subject to mildew, as compared with other varieties grown under comparable cultural conditions at Ontario, California.

Growth:

*Habit.*—Bushy; semi-upright; much branched.

*Growth.*—Vigorous.

*Canes.*—From medium caliper to heavy.

*Main stems.*—Color—between Rainette Green, Plate XXXI (Ridgway) and Light Cress Green, Plate XXXI (Ridgway). Large prickles—many; medium length; hooked slightly downward; with short, moderately round base; color—near Light Drab, Plate XLVI (Ridgway). Small prickles—none. Hairs—none.

*Branches.*—Color—near Biscay Green, Plate XVII (Ridgway). Large prickles—several; medium length; hooked slightly downward; with moderately narrow base of medium length; color—near Sayal Brown, Plate XXIX (Ridgway). Small prickles—very few; color—near Sayal Brown, Plate XXIX (Ridgway). Hairs—none.

*New shoots.*—Color—between Scheele's Green, Plate VI (Ridgway) and Peacock Green, Plate VI (Ridgway). Large prickles—few; from short to medium length; straight; with narrow base of medium length; color—near Cacao Brown, Plate XXVIII (Ridgway). Small prickles—few; color—near Cacao Brown, Plate XXVIII (Ridgway). Hairs—none.

I claim:

A new and distinct variety of rose plant of the hybrid tea class, substantially as herein shown and described, characterized particularly as to novelty by its unique combination of vigorous and floriferous habits of growth, a habit of bearing flowers on single stems ranging in length from medium to long, a graceful, urn-shaped bud form, a half-open flower form approaching that of "Charlotte Armstrong" (Plant Patent No. 455), an open-flower form approaching that of "Peace" (Plant Patent No. 591), large double flowers, and a distinctive general color tonality of the flowers ranging between White and Pale Yellow, often with tinges of Pale Pink.

No references cited.